US010144680B2

(12) United States Patent
Wang et al.

(10) Patent No.: US 10,144,680 B2
(45) Date of Patent: Dec. 4, 2018

(54) PROCESS FOR PRODUCING LIGHT OLEFINS

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Xin Wang, Beijing (CN); Jingchuan Yu, Beijing (CN); Minggang Li, Beijing (CN); Jianhong Gong, Beijing (CN); Baoning Zong, Beijing (CN); Youhao Xu, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

(*) Notice: Subject to any disclaimer, the term of this patent is extended or adjusted under 35 U.S.C. 154(b) by 0 days.

(21) Appl. No.: 15/520,721

(22) PCT Filed: Oct. 20, 2015

(86) PCT No.: PCT/CN2015/000704
§ 371 (c)(1),
(2) Date: Apr. 20, 2017

(87) PCT Pub. No.: WO2016/061905
PCT Pub. Date: Apr. 28, 2016

(65) Prior Publication Data
US 2017/0313636 A1    Nov. 2, 2017

(30) Foreign Application Priority Data

Oct. 20, 2014  (CN) .......................... 2014 1 0557715
Oct. 20, 2014  (CN) .......................... 2014 1 0557916

(51) Int. Cl.
*C07C 5/32* (2006.01)
*C07C 5/327* (2006.01)
(Continued)

(52) U.S. Cl.
CPC ............ *C07C 5/3335* (2013.01); *C07C 5/333* (2013.01); *C07C 5/3337* (2013.01); *C07C 11/02* (2013.01);
(Continued)

(58) Field of Classification Search
CPC . C07C 5/3335; C07C 5/3337; C07C 2523/86; C07C 2521/04; C07C 2529/00; C07C 2523/62
See application file for complete search history.

(56) References Cited

U.S. PATENT DOCUMENTS 3,888,764 A * 6/1975 Greenwood ............. B01J 23/90
                                                    208/140
5,049,360 A * 9/1991 Harandi ............... C10G 11/182
                                                    422/141
(Continued)

FOREIGN PATENT DOCUMENTS

CN       1213662 A    4/1999
CN       1388216 A    1/2003
(Continued)

*Primary Examiner* — Youngsul Jeong
(74) *Attorney, Agent, or Firm* — Novick, Kim & Lee, PLLC; Allen Xue (57) ABSTRACT

Disclosed is a process for producing light olefins. In the process for producing light olefins by continuously bringing an alkane feedstock and a catalyst into contact to subject to a dehydrogenation reaction, the reaction pressure P of the dehydrogenation reaction is made 0.6-2 MPa and the volume space velocity H of the dehydrogenation reaction is made 500-1000 $h^{-1}$. The light olefins production process of the present invention is simple and continuous in operation (Continued)

and has the characteristics of low investment, significant increase in yield of light olefins and high safety.

18 Claims, 3 Drawing Sheets

(51) Int. Cl.
*C07C 5/333* (2006.01)
*C07C 11/02* (2006.01)
(52) U.S. Cl.
CPC ...... *C07C 2521/04* (2013.01); *C07C 2523/62* (2013.01); *C07C 2523/86* (2013.01); *C07C 2529/00* (2013.01)

(56) References Cited

U.S. PATENT DOCUMENTS

| | | | |
|---|---|---|---|
| 5,365,006 A * | 11/1994 | Serrand | B01J 8/067 422/139 |
| 6,916,756 B2 * | 7/2005 | Schindler | B01J 23/90 502/38 |
| 7,235,706 B2 | 6/2007 | Iezzi et al. | |
| 8,282,887 B2 * | 10/2012 | Myers | B01J 8/1836 208/146 |
| 2014/0018594 A1 * | 1/2014 | Palo | B01D 53/22 585/655 |

FOREIGN PATENT DOCUMENTS

| | | |
|---|---|---|
| CN | 1952060 A | 4/2007 |
| CN | 101481289 A | 7/2009 |
| CN | 101658799 A | 3/2010 |
| CN | 102746081 A | 10/2012 |
| CN | 103121892 A | 5/2013 |
| CN | 103420750 A | 12/2013 |
| CN | 103787810 A | 5/2014 |
| EP | 0894781 A1 | 2/1999 |

* cited by examiner

PROCESS FOR PRODUCING LIGHT OLEFINS

TECHNICAL FIELD

The present invention relates to a process for producing light olefins from an alkane feedstock. Specifically, the present invention relates to a process for increasing the output of light olefins in a process for producing light olefins from an alkane feedstock.

BACKGROUND OF THE INVENTION

Lower olefins (C2-C4 olefins) are the fundamental starting materials for the organic chemical industry, and have an important role in the modern petroleum and chemical industry. As the production process, the technology of using an alkane feedstock to produce light olefins becomes more and more popular. At present, the reactor used in the technology of producing light olefins with an alkane feedstock mainly includes the fixed bed reactor and the fluidized bed reactor. The fixed bed reactor has the disadvantage of the heat transfer effect being poor, the catalyst replacement and regeneration being complex and complicated, the continuous reaction being difficulty conducted, and the like, and the advantage of being capable of achieving a large throughput of an alkane feedstock. In addition, the fluidized bed reactor can solve the aforementioned disadvantage of the fixed bed reactor, but has a much smaller throughput than the fixed bed reactor for the same reactor size as that of the fluidized bed reactor. For example, EP0894781A1 and U.S. Pat. No. 7,235,706B2 disclose processes for producing light olefins by the dehydrogenation of an alkane feedstock, wherein the fluidized bed reactors and the regenerators are used, wherein the reaction temperature is 450-800° C., the reaction pressure is 0.01-0.3 MPa, and the volume space velocity is 100-1000 $h^{-1}$.

It is known that the reaction producing light olefins with an alkane feedstock is a reaction in which the amount of molecules increases, and therefore the lower reaction pressure is favorable for the chemical equilibrium to proceed toward the production of light olefins. In view of this, in the production of light olefins according to the prior art, a lower reaction pressure is usually used in order to obtain a desired yield of light olefins. This lower reaction pressure (typically 0.1-0.3 MPa) directly results in that if desired to increase the throughput of the alkane feedstock (for example, to achieve the feedstock throughput equivalent to that of the fixed bed in the prior art) in order to increase the output of light olefins, the prior art will therefore have to increase the size or amount of the reactor so as to maintain the yield of light olefins at an acceptable level. Obviously, this will accordingly increase the investment and maintenance cost of the plant.

In the process for producing light olefins according to the prior art, in order to guarantee a continuous production process, the catalyst is circulated between the reactor and the regenerator. In order to facilitate the circulation, the reactor and the regenerator are generally operated at the substantially same pressure. Under this situation, the reactor is in a hydrogen atmosphere (a reducing atmosphere), and the regenerator is in an oxygen-containing atmosphere. If the reactor and the regenerator are not well segregated, there will be a large potential safety hazard.

In addition, a cyclone similar to that used in the catalytic cracking unit is widely used in the plant for producing light olefins according to the prior art. Therefore, it is inevitable for the catalyst natural loss during the production, in particular in case that the catalyst fine powder having a particle size of less than 20 microns becomes more and more in the catalyst. This will have a detrimental effect on the subsequent product separation, and will be adverse for the catalyst to be reused.

SUMMARY OF THE INVENTION

The purpose of the present invention is to provide a process for producing light olefins, which process overcomes the foresaid disadvantages in the prior art and is capable of directly utilizing the existing reactor and easily achieving the purpose of increasing the output of light olefins.

The present inventors have surprisingly found through an industrious investigation that if increasing the reaction pressure and correspondingly and simultaneously increasing the volume space velocity of an alkane feedstock, the yield of light olefins can be maintained at a level which is comparable to or even higher than that of the prior art, instead decreases as previously expected in the prior art, resulting in that for an existing reactor, the technical solution of increasing the reaction pressure and the volume space velocity of the reactor according to the present invention will remarkably increase the throughput of the alkane feedstock in the reactor and accordingly increase the output of light olefins (i.e. increase the output of light olefins). This finding made by the present inventions breaks through the routine knowledge of those skilled in the art, and therefore accomplishes the present invention based on this finding.

Specifically speaking, the present invention relates to the following contents.

1. A process for producing light olefins (or increasing the output of light olefins), wherein in the process for producing light olefins by continuously contacting an alkane feedstock and a catalyst to conduct a dehydrogenation reaction, the reaction pressure P of the dehydrogenation reaction is 0.4-6 MPa, preferably 0.4-3 MPa, more preferably 0.5-2 MPa, most preferably 0.6-2 MPa, the volume space velocity H of the dehydrogenation reaction is 100-5000 $h^{-1}$, preferably 200-2000 $h^{-1}$, most preferably 500-1000 $h^{-1}$.

2. The process according to any of previous aspects, wherein during the dehydrogenation reaction, H and P satisfy a mathematical function of H=f(P), which is a strictly increasing function, wherein P (unit: MPa) is in the interval [0.4, 6.0], preferably in the interval [0.4, 3.0], more preferably in the interval [0.5, 2.0], most preferably in the interval [0.6, 2.0], H (unit: $h^{-1}$) is in the interval [100, 5000], preferably in the interval [200, 2000], most preferably in the interval [500, 1000].

3. The process according to any of previous aspects, comprising the following steps:

continuously contacting the alkane feedstock and the catalyst to conduct the dehydrogenation reaction to obtain a light olefins-rich hydrocarbon and a spent catalyst, transporting at least a part of the spent catalyst to the regeneration reaction to obtain a regenerated catalyst, and circulating at least a part of the regenerated catalyst to the dehydrogenation reaction, wherein the reaction pressure P of the dehydrogenation reaction is at least 0.3 MPa, preferably 0.5 MPa, 0.7 MPa, 0.9 MPa, 1.2 MPa or 2.0 MPa higher than the regeneration pressure of the regeneration reaction.

4. The process according to any of previous aspects, wherein one or more reactors are used for the dehydrogenation reaction, and each independently selected from a fluidized bed reactor, a dense bed reactor, a riser reactor, an ebullated bed reactor and a combination thereof, preferably selected from a fluidized bed reactor, more preferably selected from a bubbling fluidized bed reactor or a turbulent fluidized bed reactor.

5. The process according to any of previous aspects, wherein the alkane feedstock is selected from at least one of C2-12 straight-chain or branched alkanes (preferably at least one of C2-5 straight-chain or branched alkanes (more preferably at least one of propane and isobutane) or a mixture of C3-12 hydrocarbons), or selected from at least one of natural gas condensate, natural gas liquid, catalytic cracking liquefied gas, oil field gas condensate, shale gas condensate, straight-run naphtha, shale oil light constituent, hydrogenated naphtha, coker gasoline and cracking gasoline.

6. The process according to any of previous aspects, wherein the catalyst is selected from at least one of a dehydrogenation catalyst, a cracking catalyst and a dehydrogenation/cracking composite catalyst.

7. The process according to any of previous aspects, wherein the reaction conditions of the regeneration reaction comprise: reaction temperature 550-750° C., preferably 600-700° C.; reaction pressure 0.1-0.5 MPa, preferably 0.1-0.3 MPa; spent catalyst residence time 5-60 minutes, preferably 6-20 minutes; oxygen-containing atmosphere, preferably air atmosphere or oxygen atmosphere.

8. The process according to any of previous aspects, wherein the spent catalyst and/or the regenerated catalyst are withdrawn by separation through a filter.

9. The process according to any of previous aspects, wherein the transporting and the circulating are performed via one or more (preferably one or two) lock hoppers (4).

10. The process according to any of previous aspects, wherein with the proviso that the size and amount of the reactors for the dehydrogenation reaction are kept the same, the process enables to increase the output of light olefins by 50%, preferably 100%, more preferably 150%, 200%, 500% or 800%, most preferably 1000% or higher.

11. The process according to any of previous aspects, further comprising a step of circulating an unconverted alkane feedstock to the dehydrogenation reaction.

12. The process according to any of previous aspects, comprising the following steps:

continuously contacting a preheated alkane feedstock and a catalyst in the reactor to conduct the dehydrogenation reaction under a dehydrogenation condition to produce the light olefins-rich hydrocarbon and the coked spent catalyst;

separating the hydrocarbon and the spent catalyst, introducing the separated hydrocarbon to a product separation-recovery system, and continuously withdrawing the spent catalyst from the reactor;

transporting the spent catalyst withdrawn from the reactor to a spent catalyst receiver, then to a spent catalyst feeding tank via a lock hopper, then to a regenerator from the spent catalyst feeding tank, and regenerating the spent catalyst in an oxygen-containing atmosphere in the regenerator to produce a regenerated catalyst;

continuously withdrawing the regenerated catalyst from the regenerator and transporting it to a regenerated catalyst receiver, then to a regenerated catalyst feeding tank via a lock hopper, and continuously transporting it back to the reactor from the regenerated catalyst feeding tank.

Technical Effects

Compared with the prior art, the process for producing light olefins according to the present invention have the following advantages.

The process for producing light olefins of the present invention, by means of increasing the reaction pressure and simultaneously and correspondingly increasing the volume space velocity of the alkane feedstock, with the proviso that the size and amount of the existing reactor or reaction plant is kept the same, enables to maintain the yield of light olefins at a level comparable to or even higher than that of the prior art, and remarkably increase the output of light olefins (e.g. by up to 1000%). Therefore, the process for producing light olefins according to the present invention is a process of increasing the output of light olefins, and can be applied to the reconstruction or upgrading of the existing light olefins production plant.

The process for producing light olefins according to the present invention, with the proviso of ensuring to achieve a predetermined output of light olefins, compared with the prior art, can remarkably reduce the size and amount of the reactor or reaction plant, and accordingly reduce the scale and investment cost of the whole light olefins production plant. Therefore, the process for producing light olefins according to the present invention is a new-generation process for producing light olefins with a high production capability, and can be applied to build a new-generation light olefins production plant with a smaller scale, a lower investment cost and a higher light olefins output than those of the existing light olefins production plant.

The process for producing light olefins according to the present invention maintains the operation of the regenerator under a lower pressure and the operation of the reactor under a higher pressure, and therefore reduces the overall complexity of the process for producing light olefins and the production plant.

The process for producing light olefins according to the present invention has a reaction pressure of the reactor remarkably higher than a regeneration pressure of the regenerator, and therefore the use of a pressure switch device (e.g. a lock hopper or a catalyst hopper) enables to implement the complete segregation of the hydrocarbon atmosphere of the reactor and the oxygen-containing atmosphere of the regenerator and accordingly ensure the overall safety of the production process and the production plant.

Other features and advantages of the present invention will be further discussed in the following part of Detailed Description of Invention.

BRIEF DESCRIPTION OF DRAWINGS

The drawings, which constitute a part of the specification, are used to provide a further understanding of the present invention, and serve to explain the present invention together with the following Detailed Description of Invention, but are not intended to limit the present invention. In the drawings.

REFERENCE IN THE DRAWINGS

1 reactor; 2 regenerator; 3 spent catalyst receiver; 4 lock hopper; 5 spent catalyst feeding tank; 6 regenerated catalyst receiver; 7 pipeline; 8 pipeline; 9 pipeline; 10 pipeline; 11 pipeline; 12 pipeline; 13 pipeline; 14 pipeline; 15 control valve; 16 control valve; 17 control valve; 18 control valve; 19 control valve; 20 control valve; 21 pipeline; 22 pipeline; 23 pipeline; 24 pipeline; 25 pipeline; 26 pipeline; 27 pipeline; 28 pipeline; 29 pipeline; 30 pipeline; 31 pipeline; 40 regenerated catalyst feeding tank; 41 pipeline; 42 pipeline; 50 plate-type grid.

DETAILED DESCRIPTION OF INVENTION

Hereinafter, the specific embodiments of the present invention will be discussed in details with reference to the drawings. It should be understood that the specific embodiments described herein are only intended to explain the present invention and the present invention is not limited thereto in any way.

In the context of the present specification, the term "yield of light olefins" refers to the once through yield of light olefins, and the term "output of light olefins" refers to the once through output of light olefins per reactor in unit time.

According to the present invention, a process for producing light olefins is provided, wherein an alkane feedstock and a catalyst are continuously contacted to conduct a dehydrogenation reaction to produce light olefins.

The process according to the present invention can comprise the following steps: continuously contacting an alkane feedstock and a catalyst to conduct the dehydrogenation reaction to obtain a light olefins-rich hydrocarbon and a spent catalyst, transporting at least a part of the spent catalyst to the regeneration reaction to obtain a regenerated catalyst, and circulating at least a part of the regenerated catalyst to the dehydrogenation reaction.

The process according to the present invention can also comprise the following steps: continuously contacting a preheated alkane feedstock and a catalyst in the reactor to conduct the dehydrogenation reaction under a dehydrogenation condition to produce a light olefins-rich hydrocarbon and a (coked) spent catalyst; separating the hydrocarbon and the spent catalyst, introducing the separated hydrocarbon to a product separation-recovery system, and continuously withdrawing the spent catalyst from the reactor; transporting the spent catalyst withdrawn from the reactor to a spent catalyst receiver, then to a spent catalyst feeding tank via a lock hopper, then to a regenerator (e.g. by stripping) from the spent catalyst feeding tank, and regenerating the spent catalyst in an oxygen-containing atmosphere in the regenerator to produce a regenerated catalyst; continuously withdrawing the regenerated catalyst from the regenerator and transporting it to a regenerated catalyst receiver, then to a regenerated catalyst feeding tank via a lock hopper, and continuously transporting it back to the reactor from the regenerated catalyst feeding tank.

The regenerator according to the present invention can be any type of the regenerators known to those skilled in the art and conventionally used in the art, for example, a fluidized bed regenerator or an ebullated bed regenerator, but not limited thereto.

It will be understood by those skilled in the art that although it is possible that active components in the catalyst can be partially oxidized after the spent catalyst is regenerated by coke-burning in the regenerator, however due to the fact that the dehydrogenation reaction of alkanes will produce hydrogen gas, even if the regenerated catalyst is not subjected to a reduction treatment before transporting back to the reactor, it can take part in the dehydrogenation reaction along with being reduced. However, in order to increase the activity of the catalyst, the process of the present invention can also comprise: transporting the regenerated catalyst withdrawn from the regenerator to a regenerated catalyst feeding tank via a lock hopper, reducing it in a reducing atmosphere to produce a reduced catalyst, and then continuously transporting the reduced catalyst back to the reactor.

The alkane feedstock according to the present invention can be C2-12 straight-chain or branched alkanes (preferably C2-5 straight-chain or branched alkanes) or a mixture thereof, for example, selected from one or more of ethane, propane, isobutane, n-butane and iso-pentane, or can be selected from at least one of natural gas condensate, natural gas liquid, catalytic cracking liquefied gas, oil field gas condensate, shale gas condensate, or can be other industrially or naturally sourced monomeric alkane feedstock or a mixture thereof.

According to the present invention, the alkane feedstock can also be a small molecule hydrocarbon mixture. As the small molecule hydrocarbon mixture, it can be a mixture of C3-12 hydrocarbons, for example, can be selected from one or more of straight-run naphtha, oil field gas condensate, shale oil light constituent, hydrogenated naphtha, coker gasoline and cracking gasoline, or can also be other industrially or naturally sourced small molecule hydrocarbon mixtures.

According to the present invention, one or more reactors can be used, which can be those well known to those skilled in the art. As the reactor, it can be a fluidized bed reactor, a dense bed reactor, a riser reactor, an ebullated bed reactor or a combination thereof, preferably a fluidized bed reactor. As the fluidized bed reactor, it is preferable to use a bubbling fluidized bed reactor or a turbulent fluidized bed reactor, more preferably a bubbling fluidized bed reactor.

According to a specific embodiment of the present invention, the fluidized bed reactor can be provided with a built-in baffle, which is in form of layers and located inside the fluidized bed reactor. The baffle can avoid the unevenly mixed flow of the hydrocarbon and/or the catalyst, and make the hydrocarbon and/or the catalyst pass through the reactor in a plug flow state to react, so as to increase the conversion rate of the alkane feedstock and the selectivity of the desired light olefins. The built-in baffle can be a plate-type grid. The plate-type grids can be provided in layers, and the distance between each two adjacent layers is 20-150 cm, preferably 50-100 cm. The distance from the bottom surface of the undermost layer of the plate-type grid to the top surface of the top layer of the plate-type grid is 5%-80%, preferably 20%-70%, further preferably 30%-50% of the total height of the inner space of the reactor. The material of the plate-type grid can be selected from the materials used for the catalytic cracking regenerator gas distributor or the large-hole distribution plate. The shape of the grid can be a wave-shape and the like. The grid can be provided with evenly distributed small or large through-holes for the regular passing of the catalyst and the gas.

In order to separate the hydrocarbon and the spent catalyst formed after the reaction in the reactor or to separate the regenerated catalyst and the fume formed after the regeneration in the regenerator, a conventional cyclone separator can be used, which is well known to those skilled in the art and therefore will not be discussed in details herein.

According to a preferred specific embodiment of the present invention, the lower olefin-rich hydrocarbon and the spent catalyst can be separated with a filter. In addition, the regenerated catalyst and the fume can be also separated with a filter. The use of the filter to separate the catalyst can effectively remove the catalyst powder and dust entrained in the hydrocarbon or the fume. Compared with the cyclone separator conventionally used in the prior art, the use of the filter can maximally reduce the natural loss of the catalyst in the production. This is one of remarkable dominances of the present invention.

According to the present invention, the filter can be a metal-sintered filter. The metal-sintered filter is a known porous material, which can effectively separate the solid powder or particles from the gas components and is robust and durable. The present invention has no specific limit to the kind and the structure of the metal-sintered filter, as long as it can effectively separate the hydrocarbon and the spent catalyst, and therefore the metal-sintered filter will not be discussed in detailed herein.

According to the present invention, the catalyst can be a dehydrogenation catalyst, a cracking catalyst, a dehydrogenation/cracking composite catalyst or a mixture thereof, and each of them can be used in the conventional type well known to those skilled in the art. The present invention has no particular limit thereto. In order to satisfy the operation requirement of the reactor and the regenerator, the catalyst is generally in a microsphere shape.

According to the present invention, the dehydrogenation catalyst generally contains an active component and a support. According to a specific embodiment of the present invention, for example, the active component can be the metal platinum or chromic oxide, and the support can be alumina; the alumina is preferably γ-Al2O3, θ-Al2O3 or a mixture of both. Based on the total weight of the catalyst, the content of the metal platinum can be 0.01 wt %-1.0 wt %, preferably 0.05 wt %-0.2 wt %. Or in case that the active component is chromic oxide, the content of chromic oxide can be 1.0 wt %-30 wt %, preferably 8.0 wt %-20 wt %. The content of the support can be a balance weight (i.e. the total weight is 100%). According to a specific embodiment of the present invention, the dehydrogenation catalyst can optionally contain ferric oxide and/or tin oxide, and can optionally contain an alkali metal oxide or an alkali-earth metal oxide. Based on the total weight of the catalyst, the content of ferric oxide and/or tin oxide can be 0 wt %-5.0 wt %, preferably 0.2 wt %-2 wt %; the content of the alkali metal oxide and/or the alkali-earth metal oxide can be 0 wt %-5.0 wt %, preferably 0.5 wt %-2 wt %. The alkali metal oxide can be for example potassium oxide, and the alkali-earth metal oxide can be for example magnesium oxide.

According to the present invention, the dehydrogenation/cracking composite catalyst is well known to those skilled in the art, and can comprise an active component, a promoter component, and a support.

Since the composite catalyst has a function for the dehydrogenation reaction and the cracking reaction, therefore the active component can comprise a dehydrogenation-function metal component and a cracking-function molecular sieve. According to a preferable embodiment of the present invention, the dehydrogenation function metal component can be one or more of Cr, Fe, Pt, Sn, Zn, V and Cu or an oxide thereof, preferably Cr or Pt and an oxide thereof. The dehydrogenation function metal component can have a weight content of 0.1-30 wt % of the total catalyst weight. The cracking function molecular sieve can be at least one of ZSM-type zeolite, Y-type zeolite and beta-type zeolite, preferably ZRP-type zeolite, and can have a weight content of 5-50 wt %, preferably 20-30 wt % of the total catalyst weight. The promoter component can be alkali metal oxide and/or alkali-earth metal oxide, preferably potassium oxide and/or magnesium oxide, and can have a weight content of 0.1-5 wt % of the total catalyst weight. The support can be an inorganic oxide, for example, at least one of alumina, silica and aluminosilicate, preferably crystal-type aluminosilicate, and can have a weight content of 15 wt %-94.8 wt % of the total catalyst weight. In order to satisfy the operation requirements of the fluidized bed reactor and the regenerator, the composite catalyst is generally in a microsphere shape, and can be prepared by the industrially common method such as spray drying and rolling into ball.

According to the present invention, in general, the reaction temperature of the dehydrogenation reaction is 500-700° C., preferably 530-600° C. In particular, in order to achieve the present inventive object of increasing the output of light olefins, the reaction pressure P of the dehydrogenation reaction is 0.4-6 MPa, preferably 0.4-3 MPa, more preferably 0.5-2 MPa, most preferably 0.6-2 MPa, and the volume space velocity H of the dehydrogenation reaction is 100-5000 $h^{-1}$, preferably 200-2000 $h^{-1}$, most preferably 500-1000 $h^{-1}$.

According to a particularly preferable embodiment of the present invention, in the dehydrogenation reaction (in other words, if intending to remarkably increase the output of light olefins upon doing a modification based on an existing reactor or reaction plant), H and P satisfy a mathematical function of H=f(P), which is a strictly increasing function. Among others, P (unit: MPa) is in the interval [0.4, 6.0], preferably in the interval [0.4, 3.0], more preferably in the interval [0.5, 2.0], most preferably in the interval [0.6, 2.0], H (unit: $h^{-1}$) is in the interval [100, 5000], preferably in the interval [200, 2000], most preferably in the interval [500, 1000]. According to this strictly increasing function, when the reaction pressure P of the dehydrogenation reaction is increased in the specific numeric interval as defined in the present invention, the volume space velocity H of the dehydrogenation reaction should be correspondingly increased in the specific numeric interval as defined in the present invention. The present invention has no limitation to the increasing manner and the increasing amplitude of the reaction pressure P and the volume space velocity H, as long as based on the normal judgement of those skilled in the art, the numerical values are indeed increased respectively; and it is not allowed to remain the numerical values unchanged or decrease the numerical values. According to one specific embodiment of the present invention, it is preferable that the reaction pressure P and the volume space velocity H are increased in proportion or in the same or different amplitude, sometimes in the same scale or synchronously, until the expected amplitude of increasing the production of light olefins is accomplished. In some cases, when the reaction pressure P arrives at the upper limit (e.g. 2 MPa) of a certain numeric interval as defined previously in the present invention, it is generally preferable that the volume space velocity H arrives at the upper limit (e.g. 1000 $h^{-1}$) of a certain numeric interval as defined previously in the present invention too, but not limited thereto.

It should be particularly noted that, when any one or both of the reaction pressure P and the volume space velocity H are not in the numeric range or the numeric interval as previously defined herein, even increasing the reaction pressure P and simultaneously and correspondingly increasing the volume space velocity H cannot obtain the effect of remarkably increasing the production of light olefins of the present invention, as shown in the Example. This is totally unexpected by those skilled in the art. According to the present invention, the regeneration reaction conditions well known to those skilled in the art can be used, and the present invention has no special limitation thereto. For example, the reaction conditions of the regeneration reaction can be: temperature 550-750° C., preferably 600-700° C.; pressure 0.1-0.5 MPa, preferably 0.1-0.3 MPa, catalyst residence time 5-60 minutes, preferably 6-20 minutes; oxygen-containing atmosphere. The oxygen-containing atmosphere can be air, a nitrogen-diluted air, an oxygen-rich gas as fluidizing medium. The preferable fluidizing medium of the regenerator is air or a nitrogen-diluted air. If necessary, a fuel gas such as finery dry gas can be supplemented in order to increase the temperature of the catalyst bed in the regenerator.

The reduction conditions can be determined based on the used catalyst, which is well known to and easily understood by those skilled in the art. It is unnecessary for the present invention to discuss this point in details. For example, the reduction condition can comprise: temperature 500-600° C., pressure 0.4-2.0 MPa, catalyst residence time 1-10 minutes. The reducing atmosphere can be a hydrogen gas-containing reducing stream as fluidizing medium. The reducing stream can be substantially free of oxygen gas, and contain 50-100 vol % of hydrogen gas and can contain 0-50 vol % of refinery dry gas. In addition, in case that using platinum as the active component of the catalyst, the long-term used catalyst needs a chlorination renovation to redistribute the platinum active centers. In this case, the regenerated catalyst feeding tank can be used as a chlorination treatment vessel.

According to a preferable embodiment of the present invention, in the process for producing light olefins from alkane feedstock as provided according to the present invention, the reaction pressure in the reactor is controlled to be at least 0.3 MPa higher than the regeneration pressure in the regenerator. Specifically speaking, the reaction pressure P of the dehydrogenation reaction is at least 0.3 MPa, preferably 0.5 MPa, 0.7 MPa, 0.9 MPa, 1.2 MPa or 2.0 MPa higher than the regeneration pressure of the regeneration reaction. Alternatively, according to the present invention, the reaction pressure P of the dehydrogenation reaction is at most 5 MPa, 3.5 MPa, 3 MPa, 2.5 MPa, 2 MPa, 1.5 MPa or 1 MPa higher than the regeneration pressure of the regeneration reaction.

According to the present invention, by means of one or more (preferably one or two) catalyst hoppers, at least a part of the spent catalyst is transported to the regeneration reaction and/or at least a part of the regenerated catalyst is circulated to the dehydrogenation reaction. According to the present invention, the lock hopper can safely and effectively transport the catalyst from a higher pressure hydrocarbon or hydrogen environment of the reactor to a lower pressure oxygen environment of the regenerator, and from a lower pressure oxygen environment of the regenerator to a higher pressure hydrocarbon or hydrogen environment of the reactor. That is to say, on one hand, the use of the lock hopper can segregate the reducing atmosphere (hydrocarbon atmosphere) in the reactor and the regenerated catalyst feeding tank for reducing the regenerated catalyst from the oxygen-containing atmosphere in the regenerator for regeneration by coke-burning, ensuring the safety of the process of the present invention; On the other hand, can flexibly adjust and control the operation pressure of the reactor and the regenerator, in particular in case of not increasing the operation pressure of the regenerator, can increase the operation pressure of the reactor and thereby increase the plant's throughput.

The lock hopper according to the present invention is any known device that can switch the same stream in different atmospheres (e.g. an oxidative atmosphere and a reducing atmosphere) and/or in different pressure environments (e.g. from a higher pressure to a lower pressure, or vice versa).

The step of transporting a catalyst from a reactor (higher pressure hydrocarbon environment) to a regenerator (lower pressure oxygen environment) through a lock hopper can comprise: 1. purging the evacuated lock hopper with a hot nitrogen to drive the residual oxygen to the regenerator; 2. purging the lock hopper with hydrogen to drive out the nitrogen; 3. pressurizing the evacuated catalyst hopper with hydrogen; 4. filling the evacuated lock hopper with the spent catalyst transported from the spent catalyst receiver; 5. depressurizing the filled lock hopper by venting hydrogen in the pressurized lock hopper; 6. purging the filled lock hopper with hot nitrogen to drive out the hydrogen; 7. discharging the spent catalyst from the filled lock hopper to the spent catalyst feeding tank. The step of circulating a catalyst from a regenerator (lower pressure oxygen environment) to a reactor (higher pressure hydrocarbon environment) through a lock hopper can comprise: 1. purging the regenerated catalyst-filled lock hopper with hot nitrogen to drive the oxygen to the regenerator; 2. purging the lock hopper with hydrogen to drive out the nitrogen; 3. pressurizing the filled lock hopper with hydrogen; 4. discharging the regenerated catalyst from the filled lock hopper to the regenerated catalyst feeding tank; 5. depressurizing the evacuated lock hopper by venting hydrogen in the pressurized lock hopper; 6. purging the evacuated lock hopper with hot nitrogen to drive out the hydrogen; 7. filling the evacuated lock hopper with the regenerated catalyst transported from the regenerated catalyst receiver. According to a specific embodiment of the present invention, only one lock hopper can be used, i.e. the spent catalyst and the regenerated catalyst use the same lock hopper for transporting, or if necessary, different lock hoppers can be used for transporting the spent catalyst and the regenerated catalyst respectively. The above variants belong to the protection scope of the present invention.

According to an embodiment of the present invention, by providing a spent catalyst receiver, a regenerated catalyst receiver, a spent catalyst feeding tank and a regenerated catalyst feeding tank, a spent catalyst from the reactor can be continuously transported to a spent catalyst receiver, then to the spent catalyst feeding tank via a lock hopper, and then continuously to a regenerator from the spent catalyst feeding tank, and a regenerated catalyst from the regenerator can be continuously transported to the regenerated catalyst receiver, then to the regenerated catalyst feeding tank via a lock hopper, then transported to the reactor from the regenerated catalyst feeding tank, so that the reaction and regeneration can be continuously conducted, wherein the regenerated catalyst feeding tank can be used as a feeding tank and as a reducer of the regenerated catalyst. In the spent catalyst receiver, the hydrocarbon contained in the spent catalyst stream can be stripped with hydrogen to the reactor in order to avoid the substance loss; in the regenerated catalyst receiver, on one hand, the catalyst in the receiver can be maintained in a fluidized state with nitrogen or other oxygen-free gases, and on the other hand, the oxygen contained in the regenerated catalyst stream is stripped to the regenerator; similarly, in the spent catalyst feeding tank, air or nitrogen can be used as a lift gas for lifting the catalyst in order to maintain the catalyst in the feeding tanker in a fluidized state.

According to the present invention, the heat required by the dehydrogenation reaction is mainly provided by the high-temperature regenerated catalyst. If required, a heating device for the feedstock and/or the catalyst being transported to the reactor can be additionally installed.

According to an embodiment of the present invention, the hydrocarbon contained in the spent catalyst stream in the spent catalyst receiver is stripped to the reactor with hydrogen.

The process according to the present invention can also comprise transporting the unreacted alkane feedstock obtained by separation from the product separation-recovery system back to the reactor.

According to the present invention, with the proviso that the size and amount of the reactors for the dehydrogenation reaction are kept the same; in other words, upon doing a modification based on an existing reactor or reaction plant, increasing the reaction pressure and the volume space velocity of the reactor in the specific ranges as defined according to the present invention can remarkably increase the throughput of the alkane feedstock of the reactor and accordingly increase the output of the light olefins. In this case, the output of light olefins can be increased by up to 50%, preferably 100%, more preferably 150%, 200%, 500% or 800%, most preferably even up to 1000% or higher.

It should be emphasized that, according to the present invention, on the basis that the yield of light olefins is kept at a level substantially identical to or slightly higher than that of the prior art, the object of increasing the output of light olefins is accomplished by increasing the throughput of the alkane feedstock of the reactor or reaction plant. Therefore, the amplitude of increasing of the output of the light olefins according to the present invention is remarkably higher, compared with the achievement of increasing the output of light olefins by simply increasing the throughput of the alkane feedstock of the reactor or reaction plant at the expense of compromising the yield of light olefins (for example, the reduction amplitude >20%). According to the present invention, the yield of light olefins can be maintained at a level comparable to or even higher than that of the prior art, for example, generally 38-55%, preferably 43-50%.

From another viewpoint, with the proviso that a predetermined output of light olefins is achieved, compared to the prior art, the production of light olefins according to the process of the present invention as defined hereinbefore can remarkably reduce the size and amount of the reactor or reaction plant, and therefore reduce the scale and investment cost of the whole light olefins production plant. The specific embodiments of the present invention will be further described with reference to the drawings, but the present invention is not limited thereto. For convenience of describing the present invention, a fluidized bed reactor is taken as an example of the reactor, but the present invention is not limited thereto.

Figure 1:
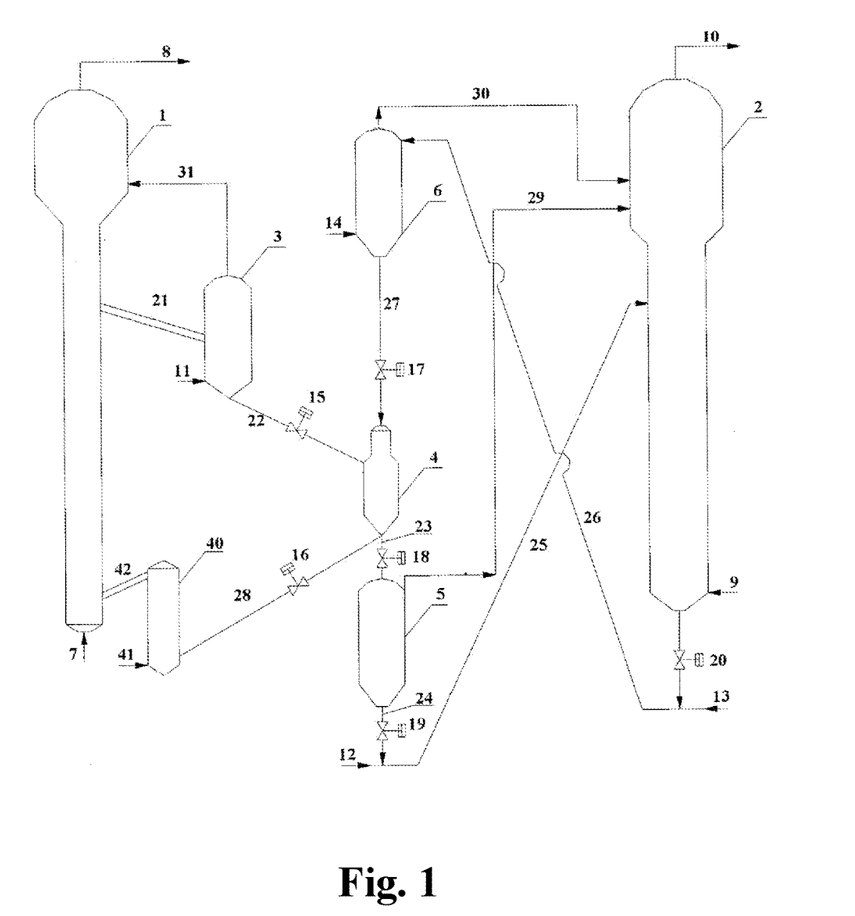
FIG. 1 is a flowchart of the process for producing light olefins according to a specific embodiment of the present invention.

The flowchart of the process for producing light olefins from the alkane feedstock as provided in FIG. 1 is as follows:

As shown in FIG. 1, a preheated feedstock is transported via the pipeline 7 and through a feedstock distributor to the fluidized bed reactor 1, contacted with a reactivated regenerated catalyst from the pipeline 28, vaporized and reacted, and then transported to the top of the reactor 1. At the top of the reactor 1, the hydrocarbon product and a small amount of catalyst particles are separated by a gas-solid separator, the catalyst particles are transported back to the reactor bed layer, and the separated dehydrogenation product is transported via the pipeline 8 to a subsequent separation system for a further separation. The spent catalyst at the upper part of the reactor is transported to the spent catalyst receiver 3 via the pipeline 21. The catalyst in the spent catalyst receiver 3 is stripped with the hydrogen from the pipeline 11 to remove the hydrocarbon, and then transported successively via the pipeline 22 and the control valve 15 to the lock hopper 4. The removed hydrocarbon is transported to the reactor 1 via the pipeline 31.

The spent catalyst is subjected to a series of purging, pressurizing, filling, depressurizing and the like in the lock hopper 4, then transported via the pipeline 23 and the control valve 18 successively to the spent catalyst feeding tank 5, then transported via the pipeline 24 and the control valve 19 successively and mixed with the air from the pipeline 12, and lifted via the pipeline 25 to the mid-top part of the regenerator 2 (e.g. the regenerator of the fluidized bed). In the regenerator 2, the spent catalyst is contacted with the oxygen-containing gas from the pipeline 9 to recover the catalyst activity by the coke-burning reaction. The regeneration fume is discharged via the pipeline 10 from the top of the regenerator 2, transported via the heat-exchanging and catalyst powder recovery system, and then vented off. The regenerated catalyst is mixed via the control valve 20 with the nitrogen from the pipeline 13, lifted via the pipeline 26 to the regenerated catalyst receiver 6. The catalyst in the regenerated catalyst receiver 6 is fluidized with the nitrogen from the pipeline 14 and stripped to remove the oxygen entrained by the catalyst, and transported successively via the pipeline 27 and the control valve 17 to the lock hopper 4.

The regenerated catalyst is subjected to a series of purging, depressurizing, filling, pressurizing and the like in the lock hopper 4, then transported successively via the control valve 16 and the pipeline 28 to the regenerated catalyst feeding tank 40, then transported via the pipeline 42 to the reactor 1, and then contacted and reacted with the feedstock from the pipeline 7.

Figure 2:
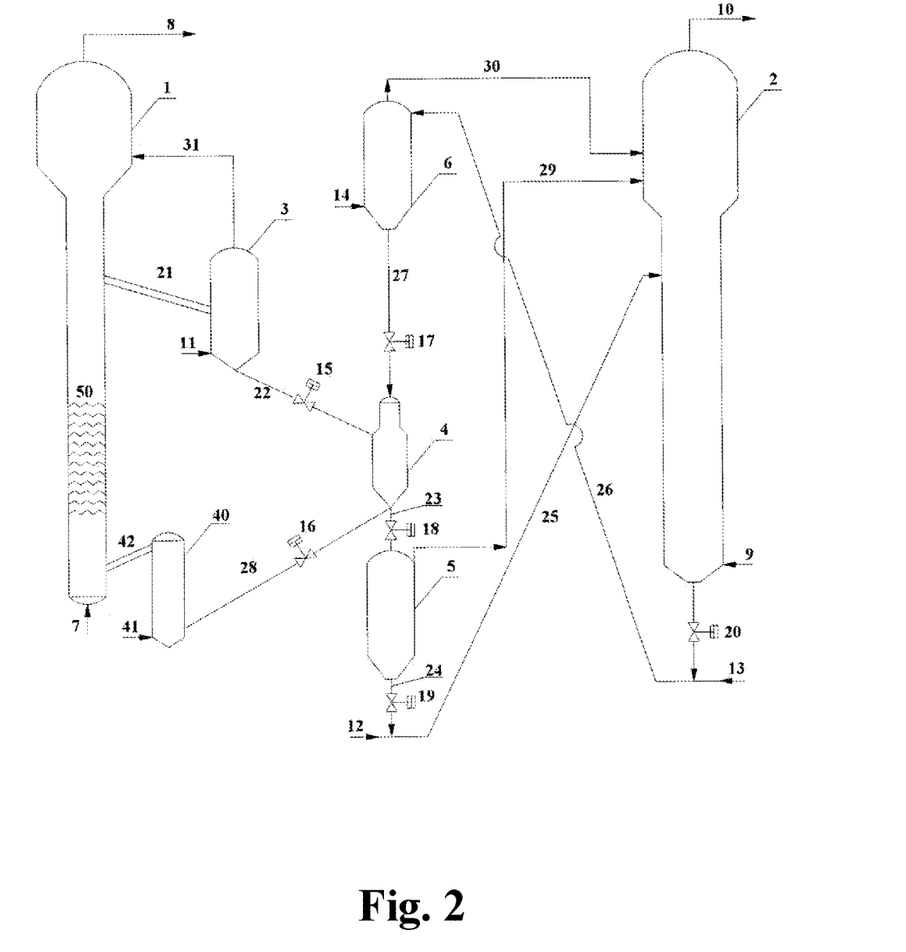
FIG. 2 is a flowchart of the process for producing light olefins according to a further specific embodiment of the present invention.
Figure 3:
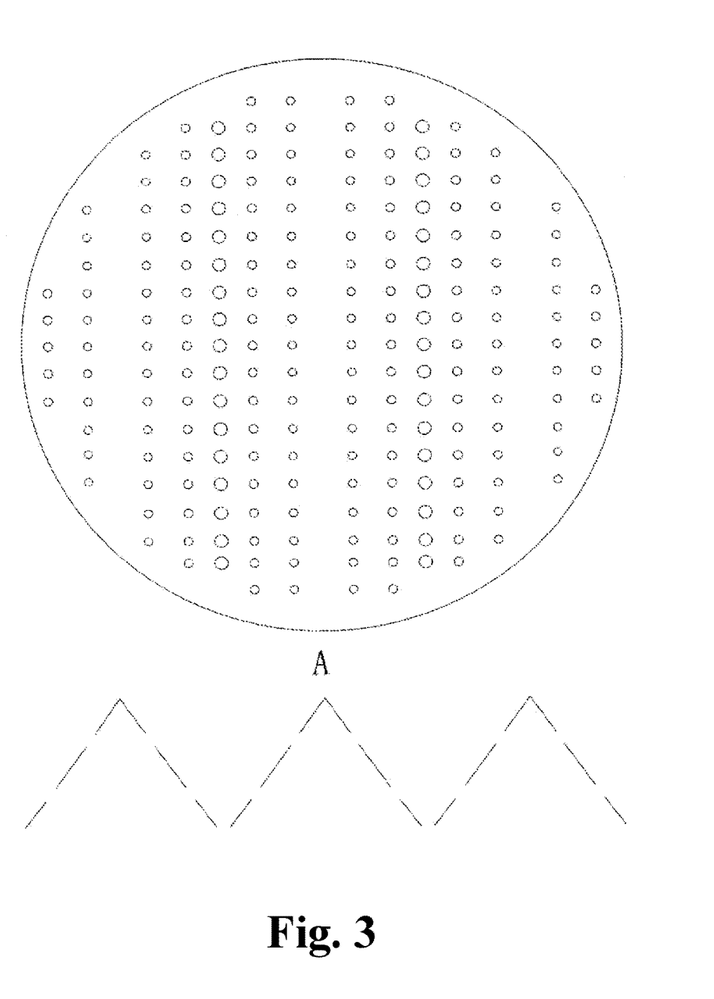
FIG. 3 shows the top view (A) and the front view (B) of an embodiment of the built-in baffle (i.e., the plate-type grid) in FIG. 2.

FIG. 2 is a further specific embodiment according to the present invention. Its flowchart is based on FIG. 1 and comprises: the regenerated catalyst is discharged from the lock hopper 4, transported successively via the control valve 16 and the pipeline 28 to the regenerated catalyst feeding tank 40, where it is reduced by a hydrogen-containing gas from the pipeline 40, and then transported via the pipeline 42 to the reactor 1, where it is contacted with the feedstock. The feedstock and the catalyst are contacted and reacted in the reactor 1, in which the plate-type grid 50 is installed.

EXAMPLE

Hereinafter, the specific embodiments of the present invention will be discussed in details with reference to the drawings.

The device used in Example was a pressurized fluidized bed device, which was similar to those shown in the drawings so as to accomplish the similar reaction and regeneration effects.

The catalysts used in Examples 1-12 and Comparative Examples 1-10 were the prepared catalysts, being a Cr—Fe—K/Al2O3 catalyst. The Cr—Fe—K/Al2O3 catalyst (hereinafter referred to as chromium-type catalyst) was prepared as follows: Firstly, 780 g of chromic nitrate (analytically pure), 100 g of ferric nitrate (analytically pure), and 80 g of potassium nitrate (analytically pure) were charged as solid to a vertical agitation tank containing 3000 g of distilled water, and the resulting mixture was stirred for 1 h; Then, 2000 g of a pre-dried γ-Al2O3 was charged to the vertical agitation tank, and the resulting mixture was adequately stirred and impregnated for 2 h; The slurry in the agitation tank was transferred to a filtering tank to filter off the excessive water, and then the catalyst was placed in a drying oven and dried at 200° C. for at least 2 h; The dried catalyst was placed in a muffle furnace and calcined at 520° C. for 6 h to produce an activated Cr—Fe—K/Al2O3 dehydrogenation catalyst, which was placed in a drier for use.

Examples 1-6

Examples 1-6 were conducted according to the process as shown in FIG. 1, the used feedstock was propane (purity=99.5% or higher), and the above Cr—Fe—K/Al2O3 dehydrogenation catalyst was used. The experiment condition, the feedstock amount, and the yield and output of light olefins were listed in Table 1.

Comparative Examples 1-4

Comparative Examples 1-4 were conducted according to the process as shown in FIG. 1, the used feedstock was propane, and the used catalysts were identical to those of Examples 1-6. The experiment condition, the feedstock amount, and the yield and output of light olefins were listed in Table 1.

Examples 7-12

Examples 7-12 were conducted according to the process as shown in FIG. 1, the used feedstock was isobutane (purity=99.5% or higher), and the above Cr—Fe—K/Al2O3 dehydrogenation catalyst was used. The experiment condition, the feedstock amount, and the yield and output of light olefins were listed in Table 2.

Comparative Examples 5-10

Comparative Examples 5-10 were conducted according to the process as shown in FIG. 1, the used feedstock was isobutane, and the used catalysts were identical to those of Examples 7-12. The experiment condition, the feedstock amount, and the yield and output of light olefins were listed in Table 2.

TABLE 1

| Example/ Comparative Example | Reaction pressure P, MPa | Feedstock volume space velocity H, $h^{-1}$ | Feedstock, kg/h | Propylene yield, % | Propylene output, kg/h |
|---|---|---|---|---|---|
| Example 1 | 0.4 | 300 | 1.2 | 42.5 | 0.51 |
| Example 2 | 0.8 | 600 | 2.4 | 43.5 | 1.04 |
| Example 3 | 1.2 | 900 | 3.6 | 43.6 | 1.57 |
| Example 4 | 1.6 | 1000 | 4 | 41.8 | 1.67 |
| Example 5 | 2 | 800 | 3.2 | 38.6 | 1.24 |
| Example 6 | 2.4 | 600 | 2.4 | 37.5 | 0.90 |
| Comparative Example 1 | 0.13 | 600 | 2.4 | 17.2 | 0.41 |
| Comparative Example 2 | 8 | 900 | 3.6 | 10.7 | 0.39 |
| Comparative Example 3 | 2 | 6000 | 24 | 7.5 | 1.80 |
| Comparative Example 4 | 1.5 | 60 | 0.24 | 21 | 0.05 |
| Comparative Example 5 | 0.13 | 100 | 0.4 | 42.6 | 0.17 |

TABLE 2

| Example/ Comparative Example | Reaction pressure P, MPa | Feedstock volume space velocity H, $h^{-1}$ | Feedstock, kg/h | iso-butylene yield, % | iso-butylene output, kg/h |
|---|---|---|---|---|---|
| Example 7 | 0.4 | 300 | 1.58 | 48.5 | 0.77 |
| Example 8 | 0.8 | 600 | 3.17 | 49.6 | 1.57 |
| Example 9 | 1.2 | 900 | 4.75 | 50 | 2.38 |
| Example 10 | 1.6 | 1000 | 5.28 | 47.6 | 2.51 |
| Example 11 | 2 | 800 | 4.22 | 45.3 | 1.91 |
| Example 12 | 2.4 | 600 | 3.17 | 44.9 | 1.42 |
| Comparative Example 6 | 0.13 | 600 | 3.17 | 18.5 | 0.59 |
| Comparative Example 7 | 8 | 900 | 4.75 | 12 | 0.57 |
| Comparative Example 8 | 2 | 6000 | 31.68 | 7.3 | 2.31 |
| Comparative Example 9 | 1.5 | 60 | 0.32 | 23.1 | 0.07 |
| Comparative Example 10 | 0.13 | 100 | 0.53 | 48.7 | 0.26 |

The catalysts used in Examples 13-18 and Comparative Examples 11-15 were the preparative dehydrogenation/cracking composite catalyst, which was prepared as follows: A certain amount of industrial-grade catalytic cracking catalyst CIP-2 (Sinopec Catalyst Co., Ltd. Qilu Division) was weighed, wherein the active component: 25 wt % of ZRP molecular sieve, the balance: aluminosilicate; then the dehydrogenation active components were impregnated onto the cracking catalyst by the impregnation method: being heated in a water bath of 60-70° C., the cracking catalyst was impregnated with a mixed solution of H2PtCl6 (analytically pure), SnCl2 (analytically pure) and MgCl2 (analytically pure), and then the catalyst was dried at 120° C. for 12 h, calcined at 550° C. for 4 h, and dechlorinated with water vapor for 2 h to produce the Pt—Sn—Mg/ZRP catalyst. Wherein the Pt content was 0.2%, the Sn content was 1%, the Mg content was 0.5%, the balance was ZRP catalyst.

Examples 13-18

Examples 13-18 were conducted according to the process as shown in FIG. 2, the used feedstock was straight-run naphtha (see Table 3), and the above Pt—Sn—Mg/ZRP catalyst was used. The experiment condition, the feedstock amount, and the yield and output of light olefins were listed in Table 4.

Comparative Examples 11-15

Comparative Examples 11-15 were conducted according to the process shown in FIG. 2. The feedstock was straight-run naphtha, and the used catalyst was identical to that used in Examples 13-18. The experiment condition, the feedstock amount, and the yield and output of light olefins were listed in Table 4.

TABLE 3

| Feedstock | Straight-run naphtha |
|---|---|
| Density (20° C.), kg/m3 | 679 |
| Initial boiling point, ° C. | 39 |
| Final boiling point, ° C. | 186 |
| Saturated vapor pressure (20° C.), KPa | 50 |
| Paraffin, wt % | 57.6 |

TABLE 3-continued

| Feedstock | Straight-run naphtha |
|---|---|
| Naphthene, wt % | 33.2 |
| Aromatics, wt % | 9.2 |

TABLE 4

| Example/Comparative Example | Reaction pressure P, MPa | Feedstock volume space velocity H, h$^{-1}$ | Feedstock, kg/h | (Ethylene + propylene) yield, % | (Ethylene + propylene) output, kg/h |
|---|---|---|---|---|---|
| Example 13 | 0.4 | 300 | 1.97 | 46.6 | 0.92 |
| Example 14 | 0.8 | 600 | 3.94 | 48.2 | 1.90 |
| Example 15 | 1.2 | 900 | 5.90 | 49.5 | 2.92 |
| Example 16 | 1.6 | 1000 | 6.56 | 45.3 | 2.97 |
| Example 17 | 2 | 800 | 5.25 | 44.1 | 2.31 |
| Example 18 | 2.4 | 600 | 3.94 | 43.9 | 1.73 |
| Comparative Example 11 | 0.13 | 600 | 3.94 | 15.6 | 0.61 |
| Comparative Example 12 | 8 | 900 | 5.90 | 10.9 | 0.64 |
| Comparative Example 13 | 2 | 6000 | 39.36 | 7.9 | 3.11 |
| Comparative Example 14 | 1.5 | 60 | 0.39 | 28.7 | 0.11 |
| Comparative Example 15 | 0.13 | 100 | 0.66 | 47.9 | 0.31 |

Example I

The feedstock used in Example I were commercially available gas products, respectively propane (purity ≥99.5%), isobutane (purity ≥99.5%), and a mixture of propane and isobutane (with a weight ratio of 1:1).

The catalysts used in Example I were respectively Cr—Fe—K/Al2O3 catalyst and Pt—Sn—K/Al2O3 catalyst.

The Cr—Fe—K/Al2O3 catalyst (hereinafter referred to as chromium-type catalyst) was prepared as follows: Firstly, 780 g of chromic nitrate (analytically pure), 100 g of ferric nitrate (analytically pure), and 80 g of potassium nitrate (analytically pure) were charged as solid to a vertical agitation tank containing 3000 g of distilled water, and the resulting mixture was stirred for 1 h; Then, 2000 g of a pre-dried γ-Al2O3 was charged to the vertical agitation tank, and the resulting mixture was adequately stirred and impregnated for 2 h; The slurry in the agitation tank was transferred to a filtering tank to filter off the excessive water, and then the catalyst was placed in a drying oven and dried at 200° C. for at least 2 h; The dried catalyst was placed in a muffle furnace and calcined at 520° C. for 6 h to produce an activated Cr—Fe—K/Al2O3 dehydrogenation catalyst, which was placed in a drier for use.

The Pt—Sn—K/Al2O3 catalyst (hereinafter referred to as platinum-type catalyst) was prepared as follows: Firstly, 20 g of chloroplatinic acid (analytically pure), 120 g of stannous nitrate (analytically pure), and 90 g of potassium nitrate (analytically pure) were charged as solid to a vertical agitation tank containing 2400 g of distilled water, and the resulting mixture was stirred for 1 h; Then 2000 g of a pre-dried γ-Al2O3 was charged to the vertical agitation tank, and the resulting mixture was adequately stirred and impregnated for 2 h; The slurry in the agitation tank was transferred to a filtering tank to filter off the excessive water, and then the catalyst was placed in a drying oven and dried at 180° C. for at least 2 h; The dried catalyst was placed in a muffle furnace and calcined at 500° C. for 4 h to produce an activated Pt—Sn—K/Al2O3 dehydrogenation catalyst, which was placed in a drier for use.

Example I-1

Example I-1 was conducted according to the process as shown in FIG. 1, the used feedstock was propane, and the prepared chromium-type catalyst and platinum-type catalyst were used respectively. The experiment condition, the conversion rate of the feedstock and the product selectivity data were listed in Table I-1.

Example I-2

Example I-2 was conducted according to the process as shown in FIG. 2, the used feedstock was isobutane, and the prepared chromium-type catalyst and platinum-type catalyst were used respectively. The experiment condition, the conversion rate of the feedstock and the product selectivity data were listed in Table I-2.

Example I-3

Example I-3 was conducted according to the process as shown in FIG. 2, the used feedstock was a mixture of propane and isobutane, and the prepared chromium-type catalyst and platinum-type catalyst were used respectively. The experiment condition, the conversion rate of the feedstock and the product selectivity data were listed in Table I-3.

It could be seen from Table I-1, Table I-2 and Table I-3 that, with the fluidized-bed reaction-regeneration system of the present invention and under the lower reaction temperature and the lower regeneration temperature, the conversion rate of the feedstock and the yield of the target olefins can reach the level of the existing industrial dehydrogenation process, and since the pressure of the reaction system is higher than that of the existing industrial plant, the feedstock throughput of the reaction system of the present invention is higher than that of the existing industrial plant under the same other operation conditions.

TABLE I-1

| Item | Data | |
|---|---|---|
| Catalyst | chromium-type | platinum-type |
| Catalyst loading, g | 2000 | 2000 |
| volume space velocity, h$^{-1}$ | 200 | 200 |
| reaction temperature, ° C. | 560 | 560 |
| reaction pressure, MPa | 1.0 | 1.0 |
| regeneration temperature, ° C. | 600 | 600 |
| regeneration pressure, MPa | 0.2 | 0.2 |
| propane conversion rate, % | 52.5 | 52.1 |
| propylene selectivity, % | 90.5 | 91.0 |
| propylene yield, % | 47.5 | 47.4 |

TABLE I-2

| Item | Data | |
|---|---|---|
| Catalyst | chromium-type | platinum-type |
| Catalyst loading, g | 2000 | 2000 |
| volume space velocity, h$^{-1}$ | 500 | 500 |
| reaction temperature, ° C. | 550 | 550 |
| reaction pressure, MPa | 0.9 | 0.9 |

TABLE I-2-continued

| Item | Data | |
|---|---|---|
| Catalyst | chromium-type | platinum-type |
| regeneration temperature, °C. | 600 | 600 |
| regeneration pressure, MPa | 0.2 | 0.2 |
| isobutane conversion rate, % | 53.6 | 53.9 |
| iso-butylene selectivity, % | 91.2 | 91.6 |
| iso-butylene yield, % | 48.9 | 49.4 |

TABLE I-3

| Item | Data | |
|---|---|---|
| Catalyst | chromium-type | platinum-type |
| Catalyst loading, g | 2000 | 2000 |
| volume space velocity, $h^{-1}$ | 700 | 700 |
| reaction temperature, °C. | 550 | 550 |
| reaction pressure, MPa | 1.0 | 1.0 |
| regeneration temperature, °C. | 610 | 610 |
| regeneration pressure, MPa | 0.2 | 0.2 |
| propane conversion rate, % | 49.6 | 50.2 |
| isobutane conversion rate, % | 50.3 | 50.9 |
| propylene yield, % | 45.5 | 45.9 |
| iso-butylene yield, % | 46.3 | 46.5 |

Example II

The feedstocks used in Examples II-1, II-2 and II-3 were respectively hydrogenated naphtha, cracking gasoline and straight-run naphtha (see Table II-1).

The dehydrogenation/cracking composite catalyst was prepared in lab as follows:

A certain amount of industrial-grade catalytic cracking catalyst CIP-2 (Sinopec Catalyst Co., Ltd. Qilu Division) was weighed, wherein the active component: 25 wt % of ZRP molecular sieve, the balance: aluminosilicate; then the dehydrogenation active components were impregnated onto the cracking catalyst by the impregnation method: being heated in a water bath of 60-70° C., the cracking catalyst was impregnated with a mixed solution of H2PtCl6 (analytically pure), SnCl2 (analytically pure) and MgCl2 (analytically pure), and then the catalyst was dried at 120° C. for 12 h, calcined at 550° C. for 4 h, and dechlorinated with water vapor for 2 h to produce the Pt—Sn—Mg/ZRP catalyst. Wherein the Pt content was 0.2%, the Sn content was 1%, the Mg content was 0.5%, and the balance was ZRP catalyst.

Example II-1

Example II-1 was conducted according to the process as shown in FIG. 1, the used feedstock was hydrogenated naphtha. The experiment condition, the conversion rate of the feedstock and the product selectivity data were listed in Table II-2.

Example II-2

Example II-2 was conducted according to the process as shown in FIG. 2, the used feedstock was cracking gasoline. The experiment condition, the conversion rate of the feedstock and the product selectivity data were listed in Table II-2.

Example II-3

Example II-3 was conducted according to the process as shown in FIG. 2, the used feedstock was straight-run naphtha. The experiment condition, the conversion rate of the feedstock and the product selectivity data were listed in Table II-2.

It could be seen from Table II-2 that, with the fluidized-bed reaction-regeneration system of the present invention and under the lower reaction temperature and the lower regeneration temperature, the yield of the cracking gas and the yield of ($C_2^=+C_3^=$) can reach the level of the existing industrial dehydrogenation, and since the pressure of the reaction system is higher than that of the existing industrial plant, the feedstock throughput of the reaction system of the present invention is higher than that of the existing industrial plant under the same other operation conditions.

TABLE II-1

| Feedstock | hydrogenated naphtha | cracking gasoline | straight-run naphtha |
|---|---|---|---|
| Density (20° C.), kg/m3 | 715 | 720 | 679 |
| Initial boiling point, °C. | 40 | 40 | 39 |
| Final boiling point, °C. | 188 | 199 | 186 |
| Saturated vapor pressure (20° C.), KPa | 53 | 54 | 50 |
| Paraffin, wt % | 58.2 | 33.5 | 57.6 |
| Naphthene, wt % | 34.2 | 12.6 | 33.2 |
| Aromatics, wt % | 7.6 | 23.6 | 9.2 |

TABLE II-2

| | Example II-1 | Example II-2 | Example II-3 |
|---|---|---|---|
| Reaction temperature, °C. | 565 | 575 | 570 |
| Reaction pressure, MPa | 0.5 | 0.9 | 0.7 |
| Feedstock volume space velocity, $h^{-1}$ | 300 | 700 | 500 |
| Regeneration temperature, °C. | 660 | 670 | 660 |
| Regeneration pressure, MPa | 0.2 | 0.2 | 0.2 |
| Cracking gas yield, wt % | 76.5 | 55.3 | 67.6 |
| Yield of ($C_2^=+C_3^=$) in the cracking gas, wt % | 49.6 | 38.9 | 46.3 |

The invention claimed is:

1. A process for producing light olefins, comprising:
    contacting an alkane feedstock and a catalyst to conduct a dehydrogenation reaction in one or more dehydrogenation reactors at a dehydrogenation reaction pressure P of 0.6-6 MPa and a volume space velocity H of 100-5000 $h^{-1}$;
    producing a light olefins-rich hydrocarbon and a spent catalyst from the one or more dehydrogenation reactors;
    transporting at least a portion of the spent catalyst to a regeneration reactor to obtain a regenerated catalyst; and
    circulating at least a portion of the regenerated catalyst to the one or more dehydrogenation reactors, wherein the dehydrogenation reaction pressure P in the one more dehydrogenation reactors is at least 0.3 MPa higher than a pressure in the regeneration reactor.

2. The process according to claim 1, wherein during the dehydrogenation reaction, H and P satisfy a mathematical function of H=f(P), which is a strictly increasing function, wherein P varies from 0.6 MPa to 6 MPa and H varies from 100 $h^{-1}$ to 1000 $h^{-1}$.

3. The process according to claim 1, wherein each of the one or more dehydrogenation reactors is independently chosen from a fluidized bed reactor, a dense bed reactor, a riser reactor, or an ebullated bed reactor.

4. The process according to claim 1, wherein the alkane feedstock comprises at least one of C2-C12 straight-chain or branched alkanes, or is selected from the group consisting of natural gas condensate, natural gas liquid, catalytic cracking liquefied gas, oil field gas condensate, shale gas condensate, straight-run naphtha, shale oil light constituent, hydrogenated naphtha, coker gasoline, cracking gasoline, and a mixture thereof.

5. The process according to claim 1, wherein the catalyst is a dehydrogenation catalyst, a cracking catalyst, or a dehydrogenation/cracking composite catalyst.

6. The process according to claim 1, wherein the regeneration reactor is maintained at a temperature of 550-750° C. a pressure of 0.1-0.5 MPa, a spent catalyst residence time of 5-60 minutes, and in an oxygen-containing atmosphere.

7. The process according to claim 1, wherein the spent catalyst is separated from the light olefins-rich hydrocarbon using a filter.

8. The process according to claim 1, wherein the transporting and the circulating are respectively performed via one or lock hoppers.

9. The process according to claim 1, wherein, with the proviso that size and amount of reactors for the dehydrogenation reaction are kept the same, the process enables to increase an output of light olefins by 50% or higher compared to a dehydrogenation reaction conducted at a pressure and a volume space velocity outside of the dehydrogenation reaction pressure and the volume space velocity recited in claim 1.

10. The process according to claim 1, further comprising a step of circulating an unconverted alkane feedstock to the one or more dehydrogenation reactors.

11. The process according to claim 1, comprising:
continuously contacting a preheated alkane feedstock and the catalyst in the one or more dehydrogenation reactors to produce the light olefins-rich hydrocarbon and the spent catalyst;
separating the light olefins-rich hydrocarbon and the spent catalyst from the one or more dehydrogenation reactors;
introducing the separated light olefins-rich hydrocarbon to a product separation-recovery system;
continuously withdrawing the spent catalyst from the one or more dehydrogenation reactors;
transporting the spent catalyst withdrawn front the one or more dehydrogenation reactors to a spent catalyst receiver, then to a spent catalyst feeding tank via a first lock hopper, then to the regeneration reactor from the spent catalyst feeding tank;
regenerating the spent catalyst in an oxygen-containing atmosphere in the regeneration reactor to produce the regenerated catalyst;
continuously withdrawing the regenerated catalyst from the regeneration reactor;
sending the regenerated catalyst to a regenerated catalyst receiver, then to a regenerated catalyst feeding tank via a second lock hopper; and
further sending the regenerated catalyst to the one or more dehydrogenation reactors from the regenerated catalyst feeding tank.

12. The process according to claim 1, wherein the dehydrogenation reaction pressure P is 0.6-2 MPa and the volume space velocity H is 500-1000 $h^{-1}$.

13. The process according to claim 1, wherein the dehydrogenation reaction pressure P in the one or more dehydrogenation reactors is at least 2.0 MPa higher than the pressure in the regeneration reactor.

14. The process according to claim 3, wherein each of the one or more dehydrogenation reactors is independently chosen from a bubbling fluidized bed reactor or a turbulent fluidized bed reactor.

15. The process according to claim 4, wherein the C2-C12 straight-chain or branched alkanes comprise propane and isobutane.

16. The process according to claim 6, wherein the regeneration reactor is maintained at a temperature of 600-700° C., a pressure of 0.1-0.3 MPa, a spent catalyst residence time of 6-20 minutes, and is maintained in air or oxygen atmosphere.

17. The process according to claim 8, wherein the transporting and the circulating are independently implemented using one or two lock hoppers.

18. The process according to claim 9, wherein the process enables to increase the output of light olefins by 100%, compared to a dehydrogenation reaction conducted at a pressure and a volume space velocity outside of the dehydrogenation reaction pressure and the volume space velocity recited in claim 1.

* * * * *